United States Patent [19]

Van Gent

[11] Patent Number: 4,955,889
[45] Date of Patent: Sep. 11, 1990

[54] APPARATUS FOR INSERTING A LENS INTO AN EYE AND METHOD FOR USING SAME

[75] Inventor: Stanley L. Van Gent, Sacramento, Calif.

[73] Assignee: Allergan, Inc., Irvine, Calif.

[21] Appl. No.: 306,103

[22] Filed: Feb. 6, 1989

[51] Int. Cl.⁵ .............................................. A61B 17/00
[52] U.S. Cl. .................................................. 606/107
[58] Field of Search ................. 128/303 R, 899, 348.1, 128/345; 606/107

[56] References Cited

U.S. PATENT DOCUMENTS

| | | |
|---|---|---|
| 4,177,526 | 12/1979 | Kuppinger . |
| 4,573,998 | 3/1986 | Mazzocco . |
| 4,575,373 | 3/1986 | Johnson . |
| 4,585,457 | 4/1986 | Kalb . |
| 4,666,445 | 5/1987 | Tillay . |
| 4,681,102 | 7/1987 | Bartell . |
| 4,699,140 | 10/1987 | Holmes et al. . |
| 4,710,194 | 12/1987 | Kelman . |
| 4,732,150 | 3/1988 | Keener, Jr. . |
| 4,743,254 | 5/1988 | Davenport . |
| 4,747,404 | 5/1988 | Jampel et al. . |
| 4,759,359 | 7/1988 | Willis et al. . |
| 4,763,650 | 8/1988 | Hauser . |
| 4,765,329 | 8/1988 | Cumming et al. . |
| 4,785,810 | 11/1988 | Baccala et al. . |
| 4,834,094 | 5/1989 | Patton et al. . |
| 4,836,201 | 6/1989 | Patton et al. . |
| 4,880,000 | 11/1989 | Holmes et al. . |

*Primary Examiner*—Michael H. Thaler
*Attorney, Agent, or Firm*—Gordon L. Peterson; Frank J. Uxa, Jr.

[57] ABSTRACT

An apparatus is disclosed for inserting a lens into an eye. The apparatus comprises a cradle acting to hold the lens, e.g., in a deformed state, prior to insertion of the lens into the eye, the cradle being constructed, preferably of a shape memory alloy, so as to release the lens in response to a change in temperature; and an insertion assembly associated with the cradle and acting to insert, and preferably withdraw, the cradle into, and preferably from, the eye.

15 Claims, 2 Drawing Sheets

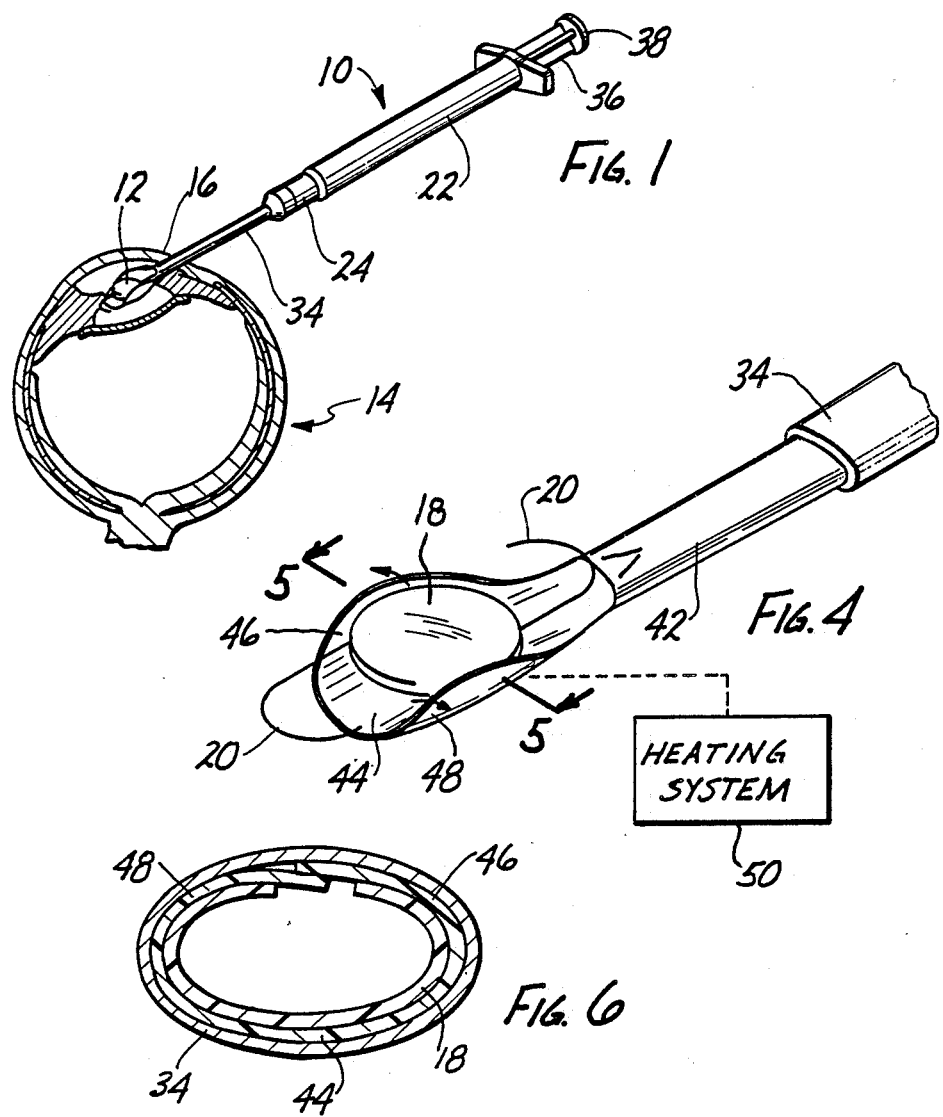
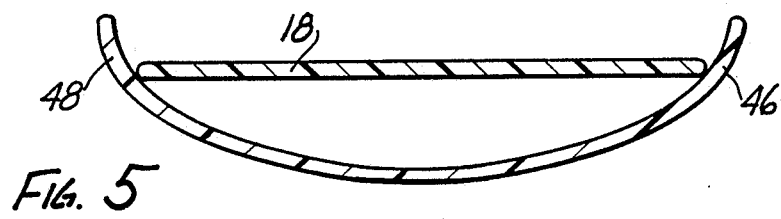

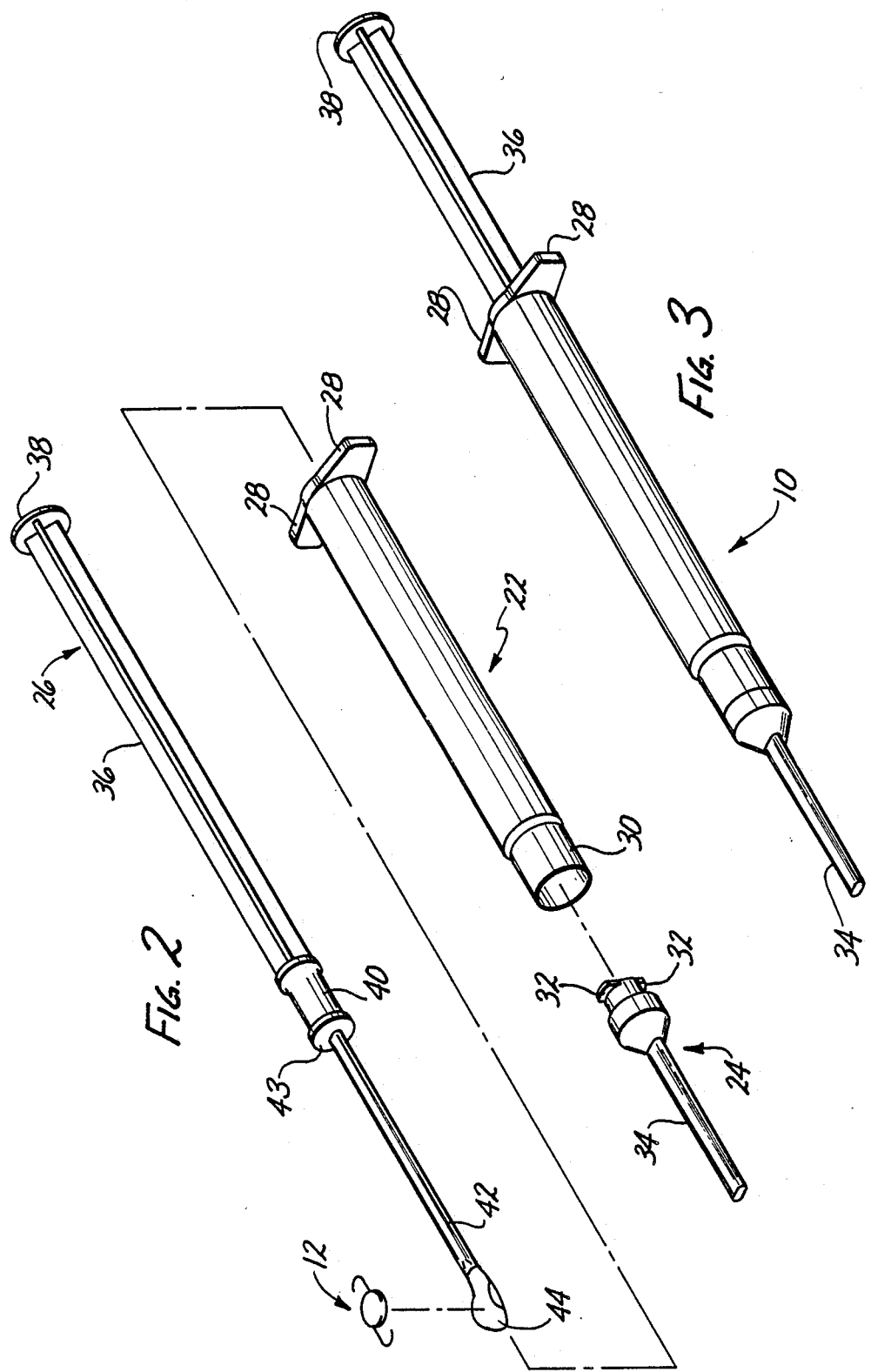

APPARATUS FOR INSERTING A LENS INTO AN EYE AND METHOD FOR USING SAME

BACKGROUND OF THE INVENTION present invention relates to an apparatus for inserting an item, e.g., an intraocular lens and the like, into an eye. More particularly, this invention relates to such an apparatus constructed so as to release the item in response to a change in temperature.

An intraocular lens is implanted in the eye, e.g., as a replacement for the crystalline lens after cataract surgery. Intraocular lenses include an optic, and preferably at least one fixation member, e.g., a haptic, that extends from the optic and becomes affixed in the eye to secure the lens in position. The optic normally includes a transparent or optically clear optical lens. Implantation of such lenses into the eye involves making an incision in the eye. It is advantageous, e.g., to reduce trauma and speed healing, to have the incision sized as small as possible.

Intraocular lenses are known which are deformable during implantation or insertion into the eye. Thus, the lens can be deformed by placing it into an insertion instrument which is then pushed through a tube located in an incision in the eye. As the insertion instrument exits the tube, the instrument opens and the lens is released into the eye. Such an inserting apparatus is disclosed in Bartell U.S. Pat. No. 4,681,102. Although such a system allows one to insert an intraocular lens through a small incision, it often provides insufficient control as to the actual position of the lens in the eye. In addition, such systems tend to be overly dependent on the technique of the individual surgeon involved. An improved insertion system would be advantageous.

Tillay U.S. Pat. No. 4,666,445 discloses an intraocular lens having a lens body, at least one flexible haptic and a component of shape memory alloy operatively connected to the haptic to change the overall dimensions of the lens for implantation of the lens. After implantation, the shape memory alloy, which is an integral part of the implanted lens, remains in the eye. The long term effects, e.g., regarding toxicity and/or other harmful effects, of the shape memory alloy in the eye remain in question. It would be advantageous to use lens materials which have been proven substantially safe when implanted in the eye.

SUMMARY OF THE INVENTION

A new apparatus and method useful for inserting an item, in particular an intraocular lens, into an eye has been discovered. This system allows the use of a relatively small incision in the eye for insertion purposes. Enhanced control of the positioning of the implanted item is also achieved. This tends to reduce the importance of the individual surgeon's technique. Moreover, the present insertion system is totally separate and apart from the item to be implanted so that the long term effects of the instrument in the eye is not an issue.

In one broad aspect of the present invention, the apparatus comprises a cradle means which is separate and apart from the item, e.g., intraocular lens, to be implanted. This cradle means acts to hold the item, preferably in a deformed configuration, prior to inserting the item into the eye. The cradle means is constructed so as to release the item in response to a change of temperature. In addition, the apparatus includes means associated with the cradle means which acts to insert the cradle means into the eye. In a particularly useful embodiment, the cradle means comprises a shape memory material.

In another broad aspect of the invention, a method for inserting such an item into an eye is involved. This method comprises placing the item into a cradle means separate and apart from the item. This cradle means is constructed, preferably of a shape memory material, so as to release the item in response to a change of temperature. The item in the cradle means is inserted into the eye and the cradle means is withdrawn from the eye after the item is released from the cradle means. The item is released from the cradle means in response to a temperature change in a controlled manner so that the item can be placed and positioned in the eye, as desired.

As noted above, the present system is useful to insert an item into an eye. In particular, this system is useful to insert an intraocular lens into an eye. The item to be inserted performs one or more useful functions in the eye. For example, an intraocular lens may be placed into the eye to replace or supplement the action of the natural lens of the eye.

The intraocular lens may be of any configuration suitable to perform the desired function in the eye. Such lenses often include a lens body or optic which has optical properties in the eye. Such lens body may have any suitable configuration. In many instances, the lens body is generally circular. However, other configurations are also useful. For example, the intraocular lens described in Davenport U.S. Pat. No. 4,743,254, which includes glare reducing sections, may be inserted into the eye using the present system. In addition, the intraocular lenses may, and preferably do, include at least one fixation member which is secured or attached to the optic. The fixation member acts to fix the intraocular lens in position in the eye. Examples of fixation members include flexible haptics which are preferably radially resilient and extend outwardly from the periphery of the lens body. Such haptics engage appropriate circumferential eye structure adjacent the iris or within the capsular bag to fix the lens in position in the eye. A very useful intraocular lens includes a plurality of, especially two, such haptics.

In order to take full advantage of the present system, it is preferred that the optic be at least partially deformable. As used herein, the term "deformable" means that the optic can be temporarily reshaped so as to pass through a smaller, e.g., in terms of diameter, incision relative to the incision required if the optic was not temporarily reshaped.

The lens body may be made of any suitable material, such as polymethylmethacrylate, silicone, hydrogel, glass or other well known materials for lens construction. Preferably, the lens body also includes an ultraviolet light absorber. The fixation member or members can be made of any suitable material, such as polymethylmethacrylate, prolene, polypropylene, nylon, silicone or other material suitable for implantation within the eye.

The cradle means acts to hold the item, e.g., the intraocular lens, to be inserted in the eye prior to such insertion. In a particularly useful embodiment, the cradle means deforms the item while holding the item. In other words, the item is preferably in a deformed configuration while being held by the cradle means. This can be accomplished by placing the item in a deformed shape into the cradle means. Alternately, the cradle means can be constructed so as to cause the deformation of the item as the cradle means takes hold of the item.

The cradle means is constructed so as to release the item from its hold in response to a change in temperature. That is, the cradle means continues to hold the item until its temperature changes and reaches a certain temperature or range of temperatures, such as the temperature in the eye. At this point, the cradle means releases the item into the eye. The cradle means is then withdrawn from the eye.

The cradle means may be of any suitable construction and/or configuration provided that it functions as described herein. Preferably, the cradle means is such that it can be withdrawn from the eye, e.g., through the incision, after releasing the item with no substantial detrimental effect on the eye or on the incision. Thus, the cradle means should be sufficiently strong and sturdy to hold the item, preferably in a deformed shape, prior to the item being released, yet sufficiently small, and preferably deformable, after the item is released to easily and effectively be withdrawn from the eye (through the incision) after the item is released.

Preferably, the cradle means comprises a shape memory material. Materials, both organic and metallic, possessing shape memory, are well known. An article made from a shape memory material can be deformed from an original, heat-stable configuration to a second, heat-unstable configuration. The article is said to have shape memory (mechanical memory) for the reason that, upon the application of heat alone, it can be caused to revert, or to attempt to revert, from its heat-unstable configuration to its original, heat-stable configuration, i.e., it "remembers" its original shape. Materials, e.g., metallic alloys, of this type are herein defined as exhibiting "temperature transition".

Among metallic alloys, the ability to display shape memory is a result of the fact that the alloy undergoes a reversible transformation from an austenitic state to a martensitic with a change in temperature. This transformation is sometimes referred to as a thermoelastic martensitic transformation. An article made from such an alloy is easily deformed from its original configuration to a new configuration when cooled to a temperature below the temperature at which the alloy is transformed from the austenitic state to the martensitic state. When an article thus deformed is warmed to a temperature at which the alloy start to revert back to the austenitic state, the deformed object will begin to return to its original configuration.

Examples of shape memory alloys exhibiting temperature transition are disclosed in U.S. Pat. Nos. 3,174,851, 3,351,463 and 3,672,879, incorporated herein by reference. A titanium-nickel-cobalt alloy is disclosed in U.S. Pat. No. 3,558,369. Suitable binary nickel-titanium shape memory alloys are well known to those skilled in the art.

In contrast to shape memory alloys exhibiting temperature transition, many shape memory alloys are known to be "pseudoelastic," displaying a reversible stress-induced martensitic state. When a shape memory alloy sample exhibiting a stress-induced martensitic state is stressed at a temperature above the temperature at which the austenitic state is initially stable, but below the maximum temperature at which formation of the martensitic state can occur even under stress, it first deforms elastically and then, at a critical stress, begins to transform by the formation of the stress-induced martensitic state. Depending on whether the temperature of the sample is above or below the temperature at which the alloy begins reverting back to the austenitic state, i.e., the reversion temperature, the behavior when the deforming stress is released differs. If the temperature is below the reversion temperature, the stress-induced martensitic state is stable; but if the temperature is above the reversion temperature, the martensitic state is unstable and transforms back to the austenitic state, with the sample returning (or attempting to return) to its original shape. The extent of the temperature range over which the stress-induced martensitic state is seen and the stress and strain ranges for the effect may vary greatly with the alloy.

In summary, it is within the scope of the invention to fabricate the cradle means of the various embodiments from shape memory materials which exhibit temperature transition or from materials which exhibit pseudoelasticity. It is preferred that the shape memory material exhibit temperature transition. The following description will generally refer to the temperature transition type material for ease of explanation.

The presently useful shape memory materials have a transition temperature or temperature range, i.e., that temperature or temperature range at which the article of shape memory material completes its revision to its original heat stable configuration, below, at or above the temperature in the eye, preferably below the temperature of the eye. For example, suppose the transition temperature is below the temperature in the eye. As the cradle means holding the item to be inserted is passed into the eye and warmed past the transition temperature, the cradle means reverts to its preset shape, releasing the item. It may be necessary to actively or positively cool the cradle means in order to deform it from its preset shape to effectively hold the item to be inserted. It may be desirable or necessary (when the transition temperature is above the temperature in the eye) to actively or positively heat the cradle means to or past the transition temperature in order to effectively release the item in the eye. This can be accomplished by associating the cradle means with a heating means effective to increase the temperature of the cradle means. Such heating means may employ electric resistance heating, microwaves and/or other energy transmitting waves, heating pads applied to the eye, etc. Care should be taken in choosing the shape memory material and in heating the cradle means to avoid temperatures in the eye which are detrimental to the eye. Choosing a shape memory material with a transition temperature below or at the temperature in the eye may avoid the potential problems caused by heating the cradle means.

The present system further includes a means or insertion assembly which acts to insert the cradle means into the eye. Preferably, this insertion assembly also acts to withdraw the cradle means from the eye, as desired. Such insertion assembly may be of any suitable configuration and construction, many of which are conventional and well known in the art. For example, the insertion assembly may include an elongated component secured to the cradle means. This elongated component is operable, preferably manually operable, to insert the cradle means into the eye. In certain embodiments, the insertion assembly may include a hollow tube through which the cradle means is passed as it is inserted into the eye. This hollow tube is preferably placed in an incision made in the eye, preferably in the iris of the eye, and allows the cradle means to be inserted into and withdrawn from the eye without damaging the eye, e.g., in proximity to the incision.

The present method of inserting an item, e.g., intraocular lens, into an eye involves placing the item in a cradle means, e.g., as described herein, inserting the item and cradle means into the eye, preferably through an incision, e.g., a relatively small incision, in the eye; and then withdrawing the cradle means from the eye after the item is released from the cradle means. Once the item is properly positioned and the cradle means is withdrawn, the incision is preferably mended, e.g., sutured, so as to facilitate healing of the incision wound.

An important feature of this invention involves the use of a cradle means, e.g., constructed of a shape memory material, which is capable of being deformed as it is withdrawn from the eye. Thus, the cradle means is preferably passed through a relatively small incision as it is inserted into the eye to deliver the item to be inserted into the eye. Once this item is released, the cradle means is withdrawn from the eye, preferably through that same relatively small incision. It has been found that the use of shape memory materials, in particular shape memory alloys, to fabricate the cradle means allows the cradle means to be deformed to such an extent that it can be withdrawn from the eye along the same path used to insert it into the eye with substantially no negative impact on the eye.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 1 is a diagrammatic view shoeing an intraocular lens being inserted into an eye, according to the present invention.

FIG. 2 is an exploded perspective view showing one embodiment of the system according to the present invention for inserting an intraocular lens into an eye.

FIG. 3 is a perspective view of the assembled system shown in FIG. 2.

FIG. 4 is a detailed perspective view of certain components of the system shown in FIG. 2 with the carrying element in the open position.

FIG. 5 is a cross-sectional view taken along line 5—5 of FIG. 4.

FIG. 6 is a cross-sectional view taken along line 5—5 of FIG. 4 with the carrying element, in the closed position, containing a folded intraocular lens.

DETAILED DESCRIPTION OF THE DRAWINGS

FIG. 1 shows the insertion apparatus, shown generally at 10, being used to insert an intraocular lens (IOL) 12 into eye 14. The IOL 12 is shown being placed by insertion apparatus 10 into an area formerly occupied by the natural lens of the eye. FIG. 1 shows the iris 16 having an incision through which the distal portion of insertion apparatus 10 may be inserted.

The IOL 12 to be inserted in accordance with the present invention includes a deformable optic 18 and two loop haptics 20, which are conventionally made of polymeric material, such as polypropylene and the like, and are very flexible. It should be noted that substantially any type of intraocular lens may be inserted using the present system, and that it is preferred that the lens be deformable. Alternate configurations of intraocular lenses useful with the present system include those described in Bartell U.S. Pat. No. 4,681,102 (e.g., web haptics) and in Davenport U.S. Pat. No. 4,743,254 (e.g., movable glare reducing sections).

As best shown in FIG. 2, insertion 10 includes a hollow cylinder 22, a distal end piece 24 and an elongated member or plunger 26. Cylinder 22 has an interior hollow space sized and adapted to receive the plunger 26, as described herein. A pair of gripping wings 28 extend radially from the proximal end of cylinder 22 and act to facilitate the manual passing of plunger 26 through the hollow space of cylinder 22. The interior of distal end portion 30 of cylinder 22 is adapted to receive and hold the proximal end of distal end piece 24. Specifically, locking projections 32 extend radially from the proximal end of distal end piece 24 and are sized and adapted to be received and held in the interior of distal end portion 30. Distal end piece 24 further includes a hollow, distally extending tube 34 which as will be described herein, is actually inserted into eye 14. Tube 34 is elliptically shaped to facilitate its insertion into eye 14. The hollow interior space within tube 34 is also elliptically shaped. With distal end piece 24 secured to cylinder 22 there is a continuous open through path from the proximal end of cylinder 22 to the distal end of tube 24.

Plunger 26 includes an elongated body element 36, an end member 38, a seal element 40, an elliptically shaped rod 42 and a carrying element 44. Elongated body element 36 is sized to move freely in an out of the hollow cylinder 22. End member 38 is secured to the proximal end of elongated body element 36 and acts to facilitate the manual insertion and withdrawal of plunger 26 into and out of cylinder 22. Seal element 40 is secured to the distal end of elongated body element 36 and is sized and adapted to move within a portion of the through path noted above. Seal element 40 fits snugly into the hollow space of cylinder 22 and, thus, acts to provide no resistance to the movement of plunger 26 within cylinder 22. Further seal element 40 acts as a stop to control the degree to which plunger 26 can be inserted into cylinder 22. Specifically, member 43, located at the distal end of seal element 40 is sized so as to be restricted from passing into distal end piece 24. This limits the extent to which plunger 26 can be inserted into cylinder 22 and thereby protects the eye 14 from accidental damage.

Rod 42 is solid, and elliptically shaped and sized so as to fit into and pass through tube 34. Rod 42 is secured to seal element 40, as shown best in FIG. 2. All the components of insertion apparatus 10 noted and described above, with the exception of carrying element 44, may be made of any suitable material or materials of construction. In one useful embodiment, these components are made of e.g, molded from, one or more polymeric materials. For example, the plunger 26 minus the carrying element 44, the cylinder 22 and the distal end piece 24 can each be molded out of the same or different polymeric materials.

Carrying element 44 is secured, e.g., by adhesive, to the distal end of rod 42. Carrying element 44 is made of a shape memory alloy which is programmed or has a composition to release the IOL 12 at the temperature within eye 14. Carrying element 44 has a transition temperature below the temperature within eye 14. Carrying element 44 is in the general shape of a spoon with side flaps 46 and 48. Many other configurations and structures are useful in the carrying element of the present invention and are, therefore, included within the scope of the present invention. For example, carrying element 44 may be made of a wire mesh or only a limited number of wires, even only one wire. The configuration of carrying element 44 is chosen based at least in part on the following criteria: first, that carrying element 44 be strong enough to hold IOL 12 in the desired, preferably deformed, configuration prior to releasing IOL 12 into eye 14; second, that carrying element 44 be small enough to pass through the incision (through tube 34) into eye 14; and third, that carrying element 44 be capable of releasing IOL 12 in eye 14 and of being withdrawn from eye 14 without undue damage to eye 14.

The shape memory alloy from which carrying element 44 is made is such that at the temperature within the eye 14, the carrying chamber 44 reverts to its original shape and opens up, i.e., side flaps 46 and 48 separate, to allow IOL 12 to be separated or released from carrying element 44. A heating system 50 may optionally be included to heat carrying element 44 to a temperature equal to or greater than the transition temperature of carrying element 44. Heating system 50 may involve electric resistance heating with wires passing through rod 42 to contact carrying element 44. Alternatively, heating system 50 may involve an energy wave generator or similar device capable of increasing the temperature of carrying element 44 without directly physically contacting carrying element 44. Heating system 50 may be heating pads or hot packs applied to the eye to increase the temperature of carrying element 50. Other embodiments of heating system 50 may be appropriate. However, care should be exercised in increasing the temperature of carrying element 44 to avoid damaging the patient, and in particular the eye 14, being treated.

Insertion apparatus 10 functions as follows. IOL 12 is placed on carrying element 44 as shown in FIGS. 4 and 5. Thus, the loop haptics 20 extend out of optic 18 in generally opposing directions, generally parallel to the longitudinal axis of rod 42. At this point, carrying element 44 is at a temperature at which carrying element 44 is easily deformed. It may be desirable or even necessary to positively cool carrying element 44 to this temperature and/or to maintain this temperature at which carrying element 44 is easily deformed. Note that the entire diameter of optic 18 fits between side flaps 46 and 48. Carrying element 44 is then manipulated, e.g., manually manipulated, to its folded shape. The folded shape, as shown in FIG. 6 is with side flaps 46 and 48 overlapped to produce a substantially elliptical cross-section perpendicular to the longitudinal axis of rod 42. In the process of being manipulated into its folded shape, carrying element 44 deforms or folds optic 18 to a configuration as shown in FIG. 6. With carrying element 44 in its folded shape (FIG. 6), it can pass through the entire through path from the proximal end of cylinder 22 to the distal end of tube 34 and beyond.

After carrying element 44 (holding IOL 12) is in its folded shape, and while maintaining a sufficiently low temperature to keep it in its folded shape, an incision is made in the iris 16 of eye 14. Tube 34 is placed in the incision. Carrying element 44 is passed through tube 34 by pushing plunger 26 into cylinder 22. As carrying element 44 emerges in eye 14 its temperature begins to approach the temperature of eye 14. Heating system 50 may be employed to assist in increasing the temperature of carrying element 44. This change in temperature past the transition temperature of carrying element 44 causes carrying element 44 to revert to its original shape, thereby releasing IOL 12 into the eye 14 at the desired position. Once the IOL 12 is released, carrying element 44, which is sufficiently flexible at the temperature of eye 14 to pass through tube 34, is easily removed from eye 14 through tube 34. One important advantage of the present system is that the IOL 12 is not unfolded immediately upon being placed in the eye 14. Some period of time is required for the carrying element 44 to open in eye 14. During this time period, while carrying element 44 is still holding IOL 12, the surgeon can manipulate insertion apparatus 10 to properly position IOL 12 in eye 14. In effect, using insertion system 10, the surgeon has more direct control of the proper placement of IOL 12 in eye 14 relative to systems in which the IOL unfolds immediately upon entering the eye. After insertion apparatus 10 is withdrawn from the eye 14, if needed, the position of the IOL 12 can be adjusted by a small, bent needle, or similar tool inserted into the same incision.

Once the IOL 12 is properly placed in eye 14 and insertion apparatus 10 is withdrawn from eye 14, the incision in the iris 16 is mended, e.g., using conventional techniques. After use, insertion apparatus 10 is preferably disposed of.

In the event that carrying element 44 is made of a shape memory alloy having a transition temperature above the temperature in the eye 14, heating system 50 is preferably employed to increase the temperature of carrying element 44 to or past this transition temperature to release IOL 12.

While this invention has been described with respect to various specific examples and embodiments, it is to be understood that the invention in not limited thereto and that it can be variously practiced within the scope to the following claims.

What is claimed:

1. An insertion apparatus for an intraocular lens comprising:
    an elongated member having opposite ends and including a carrying element at or adjacent one of said ends;
    said carrying element being adapted to hold an intraocular lens and sized and adapted for insertion through an incision into a human eye;
    said carrying element being constructed of a shape memory material and having an original open configuration in which the carrying element is adapted to receive an intraocular lens;
    said carrying element being deformable from said original configuration to a folded configuration in which the carrying element is adapted to capture the intraocular lens;
    said carrying element returning to said original shape in response to a temperature change whereby inserting of the carrying element through the incision into the eye with the carrying element in said folded configuration and subjecting the carrying element to said temperature change causes the carrying element to return to said original configuration and release the intraocular lens into the eye.

2. The apparatus of claim 1 wherein said shape memory material has a transition temprature and which further comprises heating means other than the patient acting to heat said carrying element to or above said transition temperature.

3. The apparatus of claim 1 wherein said shape memory alloy has a transition temperature below the temperature in said eye.

4. The apparatus of claim 1 wherein said shape memory alloy has a transition temperature above the temperature in said eye.

5. The apparatus of claim 1 including a hollow tube through which said carrying element is passed.

6. The apparatus of claim 1 including an elongated tube receiving said elongated member therein for movement of the elongated member longitudinally relative to the elongated tube, said elongated tube having a distal end and said carrying element in said folded configuration being receivable in said elongated tube and extendable out of the distal end of said elongated tube.

7. The apparatus as of claim 1 wherein the carrying element is at said one end of the elongated member.

8. A method for inserting an intraocular lens through an incision into an eye of a patient comprising:
providing a carrying element of shape memory material having an original open configuration in which the carrying element is adapted to receive an intraocular lens;
placing the intraocular lens on the carrying element;
deforming the carrying element into a folded configuration in which the carrying element captures the intraocular lens;
inserting the carrying element in the folded configuration with the intraocular lens captured by the carrying element through the incision into the eye of the patient and raising the temperature of the carrying element sufficiently to cause the carrying element to return to said open configuration whereby the introacular lens is released in the eye; and withdrawing the carrying element from the eye.

9. The method of claim 8 wherein said shape memory material has a transition temperature above the temperature in said eye and including heating said carrying element in said eye to a temperature at or above said transition temperature.

10. The method of claim 8 wherein said shape memory material has a transition temperature range below the temperature in said eye.

11. The method of claim 8 wherein said shape memory material has a transition temperature range above the temperature in said eye.

12. The method of claim 8 wherein said inserting step includes passing said carrying element through a hollow tube placed in said incision.

13. The method of claim 8 wherein said carrying element is deformed as said carrying element, is withdrawn from said eye.

14. The method of claim 8 which further comprises reducing the temperature of said carrying element to a reduced temperature and carrying out said step of placing with the carrying element at said reduced temperature.

15. The method of claim 8 wherein the intraocular lens is deformable and said step of deforming causes the carrying element to deform the intraocular lens.

* * * * *